United States Patent

Pliura et al.

[11] Patent Number: 5,439,591
[45] Date of Patent: Aug. 8, 1995

[54] DISPLACEMENT CHROMATOGRAPHY PROCESS

[75] Inventors: Diana Pliura, Mississauga; Diane Wiffen, Georgetown; Salman Ashraf, Mississauga; Anthony Magnin, Willowdale, all of Canada

[73] Assignee: Hemosol Inc., Etobicoke, Canada

[21] Appl. No.: 187,316

[22] Filed: Jan. 27, 1994

[30] Foreign Application Priority Data

Sep. 21, 1993 [CA] Canada ................... 2106612

[51] Int. Cl.⁶ ............................................. B01D 15/08
[52] U.S. Cl. ................................. 210/635; 210/656; 210/198.2; 530/385; 530/413; 530/416; 530/417
[58] Field of Search ............ 210/635, 656, 659, 198.2; 530/385, 413, 416, 417

[56] References Cited

U.S. PATENT DOCUMENTS

| | | | |
|---|---|---|---|
| 3,971,842 | 7/1976 | Ewbank | 210/656 |
| 4,599,175 | 7/1986 | Yamamizu | 210/635 |
| 4,764,279 | 8/1988 | Tayot et al. | 210/656 |
| 4,925,574 | 5/1990 | Hsia | 210/635 |
| 5,028,696 | 7/1991 | Torres | 210/656 |
| 5,043,423 | 8/1991 | Viscomi | 530/344 |
| 5,084,558 | 1/1992 | Rausch | 530/385 |
| 5,149,436 | 9/1992 | Taniguchi | 210/656 |
| 5,264,555 | 11/1993 | Shorr et al. | 530/385 |
| 5,340,474 | 8/1994 | Kauvar | 210/198.2 |

OTHER PUBLICATIONS

Christensen, "Preparation of Human Hemoglobin Ao for Possible Use as a Blood Substitute," J. Biochem. Phys. 17 (1988), pp. 143–154.

Primary Examiner—Ernest G. Therkorn
Attorney, Agent, or Firm—Ridout & Maybee

[57] ABSTRACT

Hemoglobin is purified from a crude solution thereof, to obtain an aqueous solution containing at least 99% of a preselected hemoglobin species, by a two stage displacement chromatography process. One of the stages is conducted under anionic exchange conditions, and the other under cationic exchange conditions. In both stages, the exchange column is overloaded to displace the hemoglobin species therefrom with contaminants having greater affinity for the column, and using the impure hemoglobin solution as the displacer. Normally, anionic exchange is conducted first, with contaminants more acidic than the hemoglobin displacing the hemoglobin from the column and themselves remaining attached to the column for separation. The cationic exchange process is conducted second, on the eluent from the first column, and in this stage, the more basic contaminants displace the hemoglobin from the column under overload conditions, to yield a substantially pure hemoglobin solution.

11 Claims, 5 Drawing Sheets

DISPLACEMENT CHROMATOGRAPHY PROCESS

FIELD OF THE INVENTION

This invention relates to hemoglobin purification by chromatography, and more particularly to chromatographic processes for purifying hemoglobin, on a commercial scale, to obtain an solution in which hemoglobin constitutes at least 99% of the solute.

BACKGROUND OF THE INVENTION AND PRIOR ART

The development of hemoglobin based blood substitutes continues to command commercial attention, and recent developments have shown that hemoglobin from mammalian blood cells, after suitable modification such as intramolecular crosslinking and in some instances polymerization, shows great promise as the basis of a blood substitute. As development has proceeded, however, the requirements for purity of the hemoglobin have steadily increased. At one time, it was believed that hemoglobin simply needed to be stroma free, a condition achievable by very gentle lysing and washing of the red blood cells. Subsequently, it was found that the presence of very small traces residues of blood cell components such as endotoxins and phospholipids led to adverse reactions of the product in animal trials. Even after the product has been subjected to several diafiltration steps, it still contains unacceptably high traces of harmful impurities such as erythrocyte enzymes, modified and variant forms of hemoglobin, phospholipids and surface antigens.

One of the most urgent challenges in the blood substitute area, specifically the hemoglobin-based oxygen carriers, is the to develop processes for efficient and economical purification of proteins on a commercial scale. The need for a cost effective and efficient purification system is perhaps the most urgent need in this area, because the manufacture of large quantities of purified hemoglobin needs also to be able to meet the required cost criteria.

Whereas resolution and analysis time are important in analytical separations, the critical parameters in preparative chromatography, for commercial or semi-commercial scale use, are:

the amount of material isolated per unit time at a specific level of purity (throughput); and economics of the process, such as column sizes, media, buffers, equipment, recycle and re-use of components and reagents and the like.

There are no reported methods for the purification of HbAo which meet the criteria for a cost efficient production process.

A hemoglobin-based blood substitute needs to be based either on a single hemoglobin form, or, if more than one form is present, a carefully controlled composition of known hemoglobin forms. Accordingly, a successful hemoglobin purification process needs to be capable of separating one hemoglobin form from another, as well as separating the desired Hb form from other contaminating red blood cells such as erythrocyte enzymes, phospholipids and surface antigens.

Chromatographic methods have been applied to the purification of hemoglobin solutions. U.S. Pat. No. 4,925,474 Hsia et al. describes the application of the techniques of affinity chromatography to hemoglobin purification, using columns in which a ligand showing preferential chemical binding affinity to the DPG site of hemoglobin was bound to the stationery phase of the column.

Ion exchange chromatographic techniques have also been applied to hemoglobin purification. The basic principles of the techniques of ion exchange chromatography are well known. A mixture of different species in a solution is applied to a suitably prepared ion exchange column. Each of the species in the mixture has a different affinity for the chemical reactant groups on the column. By varying the conditions on the column, e.g. the pH of the solution, the individual species can be arranged to bind or to elute from the column selectively, so as to separate the species individually from the mixture. The application of the technique to the purification of proteins such as hemoglobin is economically unattractive, except when used for small scale operations and analytical work. When hemoglobin is to be purified on a commercial scale, for use for example as an oxygen carrying rescusitative fluid (blood substitute), the technique as conventionally applied is impractical. The amounts of hemoglobin to be absorbed on and subsequently eluted from a chromatography column are so large that the column size requirements become impractically large and expensive.

Christensen et al., J. Biochem. Phys. 17 (1988), 143-154, reported the chromatographic purification of human hemoglobin. The methodology used represented a standard ion exchange chromatographic approach that did not provide opportunities for economical scale-up to production levels.

U.S. Pat. No. 5,084,588 Rausch and Feola (Biopure), describes standard anion and cation exchange chromatography methods for application to separation and purification of hemoglobin. In the case of anion exchange chromatography, three standard approaches are listed in this patent:

a) binding of the Hb at elevated pH, and elution with a descending pH gradient or step gradient of lower pH;

b) binding of the Hb at high pH, low ionic strength and elution with a salt gradient;

c) loading under pH conditions where the hemoglobin does not bind to the anion exchanger, but passes through the column unretained, while the impurities (more acidic contaminants) are captured on the column.

Approaches a) and b) have been extensively documented, but are not attractive for large scale production, owing to the limitation of low loading capacities necessary to achieve sufficient resolution of the hemoglobin products. These loading capacities are routinely only 20-30 mg/ml, which dictate prohibitively large and expensive columns for commercial scale purification of hemoglobin. For example, each 50 gm dose of final hemoglobin-based oxygen carrier (HBOC) would require a column of 1.5-2.5 liters.

Whilst approach c) would appear on the surface to be the most pragmatic, it turns out in practice that the chromatographic properties of human adult, normal, unmodified hemoglobin HbAo and some of the major contaminants such as HbAlc are not sufficiently distinct for practical application of this approach.

The standard approaches to cation exchange chromatography of mammalian hemoglobin have similar limitations.

SUMMARY OF THE INVENTION

It is an object of the present invention to provide a novel chromatographic process for the purification of hemoglobin.

It is a further object of the invention to provide a chromatographic process capable of yielding, on a commercial scale and in an economically acceptable fashion, hemoglobin in aqueous solution in a purity in excess of 99%, from a contaminated aqueous solution thereof containing at least 60% of hemoglobin.

It is a further and more specific object of the present invention to provide, in commercial quantities, an aqueous solution of hemoglobin or crosslinked hemoglobin of which the hemoglobin or crosslinked hemoglobin constitutes at least 99% of the solute, and is in a state of purity heretofore unreported.

The present invention provides a process whereby an aqueous solution of preselected hemoglobin species, Hb, in which the Hb constitutes from about 60% to about 95% of the dissolved material, is subjected to ion exchange chromatography in two stages. One of the stages is an anionic exchange chromatography, and the other of the stages is a cationic exchange chromatography. The two types of ionic exchange chromatography can be conducted in either order. A crude solution of the preselected hemoglobin species Hb is fed to the first stage of chromatography, for example anionic exchange chromatography under conditions chosen so that all the constituents of the mixed solute are absorbed on the solid phase of the chromatographic column initially. For anionic exchange, this requires a relatively high pH. The conditions are also chosen so that very high, very effective loading of the column is achieved, using low ionic strength of feed solution, leading to a situation in which substantially all of the accessible sites on the solid chromatographic medium are occupied by species of the feed solution. Eluent collected at this stage is devoid of protein product. Displacement of Hb and the contaminants having lower affinity for the column under the chosen conditions is then achieved by loading additional volumes of aqueous feed solution as defined above. The condition thereby achieved, herein referred to as an overload condition, causes contaminant species of greater affinity for the column to displace the Hb and the contaminant species of lesser affinity for the column, to be eluted from the column. When this first stage chromatographic separation is anionic exchange chromatography, contaminants which are more acidic than the selected Hb species are absorbed on the solid phase of the chromatographic column, and are thereby separated from the selected Hb species, which appears in the eluent along with the more acidic contaminants. In the case where cationic exchange chromatography is selected as the first stage, the more basic contaminants are separated, by greater affinity to the column, with the more acidic contaminants and the selected hemoglobin species appearing in the eluent.

Then, in the second chromatographic stage of the process of the invention, a second ionic exchange chromatography is conducted, on the impure hemoglobin species containing solution from the first column, under the opposition conditions. When the eluent from the first column contains the hemoglobin species and the more basic constituents, the second stage chromatography is cationic exchange chromatography, and visa versa. The feed of this impure solution to the second column is again conducted until saturation loading is reached, and exceeded, so as to create an overload condition in the column. At the overload condition, the preselected hemoglobin species is eluted from the column by displacement by the contaminants of greater affinity under the chosen conditions, and the hemoglobin species is thereby collected in the eluent from the second column, in a very high state of purity. The process of the invention may thus generally be called "two stage self-displacement chromatography".

As a result, the Hb species is eluted from the column, in exceptional pure form, normally in excess of 99% purity and in commercially attractive yields. Contaminants more acidic than the selected Hb species remain attached to one column resin, and contaminants more basic than the selected Hb species remain attached to the other column resin. The columns can be easily regenerated using traditional cleaning and regeneration procedures.

An important factor in the successful operation of the process, especially on a large, commercial scale, is the selective, high loading of the columns with the impurities, allowing the Hb species to elute.

BRIEF REFERENCE TO THE DRAWINGS

Figure 1:
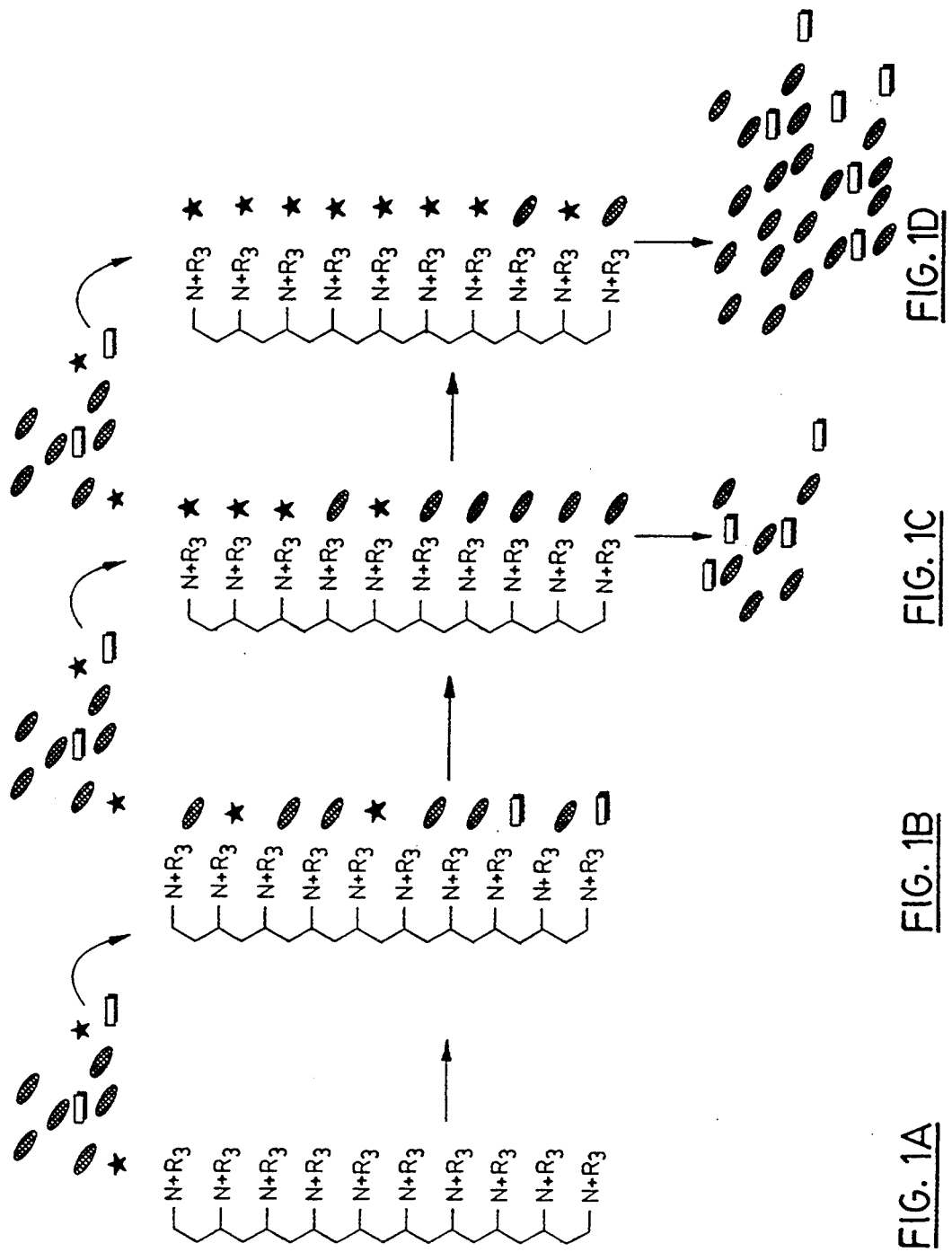
FIGS. 1A–1D are diagrammatic illustrations of the initial, anionic exchange portion of the preferred process of the present invention.

DESCRIPTION OF THE PREFERRED EMBODIMENTS.

Displacement chromatography, or displacement elution as it is commonly termed, is a known technique, in the field of protein separation. It is one of the three modes by which a sample is recovered from a chromatography column. As applied to protein separations from a mixture of proteins in solution, proteins of greater affinity will displace proteins of lesser affinity on the matrix, so that a hierarchy of proteins in descending order of affinity is set up within the column, from inlet to outlet. When proteins displace other proteins, a sharp line of demarcation between the species is rarely formed. The application of the technique to prepare highly pure solutions of a single protein such as a hemoglobin is thus contraindicated. If a separate, non-proteinaceous displacing species is chosen, the result may be the formation of a gel having bound to it a substance of very high affinity for the gel, which is very difficult to clean up ready for reuse.

The process shows its chief commercial utility in preparation of purified adult human hemoglobin HbAo, and so it will be particularly described with reference thereto, for convenience. The process is not, however, restricted to HbAo purification, but is additionally applicable to other preselected hemoglobin species such as selected bovine hemoglobin variants, other hemoglobin variants, such as fetal hemoglobin, sickle cell hemoglobin etc., genetically engineered hemoglobin, etc.

The process of the invention is extremely attractive economically, for use to purify hemoglobin HbAo on a commercial scale to produce blood substitutes. It uses very high column loading. It can consequently utilize relatively small size columns, to purify relatively large volumes of impure hemoglobin solution. It can be run continuously to purify a given batch of hemoglobin solution as obtained from red blood cells by standard techniques, solutions which normally contain of the order of 80% hemoglobin, but which contain a wide variety of impurities, both proteinaceous and non-proteinaceous. Moreover, the impure hemoglobin solution itself is used as the displacement medium. The provision and use of a separate displacer, with its attendant inconveniences, complications and expense, is thereby avoided.

A typical overall process for making a purified HbAo solution involving the technique of the present invention starts with adult, human red blood cells. These are pooled and subjected to filtration to remove leukocytes. Then they are lysed to extract the hemoglobin and other cell components. The product is washed to remove plasma proteins and red blood cell (RBC) proteins present as a result of the hemolysis. The resultant hemoglobin solution is diafiltered and concentrated. Then the impure hemoglobin component is treated with carbon monoxide to form a CO—Hb complex and heated to pasteurize it, thereby inactivating viral contaminants in the solution. It is then centrifuged and filtered, to remove further remnants of cellular debris. It may be subjected to a chemical crosslinking step after pasteurization. It is now ready to be subjected to the self-displacement process of the present invention.

According to the preferred embodiment of the invention, the first stage of the chromatographic process is the anionic exchange process, and the second stage is the cationic exchange process. This first, anionic exchange process is preferably run at high pH, e.g. pH 7–10 and preferably pH 8.5–9.0, and under conditions of low ionic concentration i.e. low conductivity. The conductivity is suitably less than 3 mS (milli Siemens) and preferably less than 1 mS. Such conditions involve an essentially salt free buffer. The desired HbAo species will initially bind to the column medium under these conditions, along with all other species. As the feed of impure HbAo solution to the column continues, those species of greater acidity, which show greater affinity than the HbAo, gradually displace the HbAo and more basic contaminants from the column. Eventually, an overload of the column is achieved, so that all the HbAo and more basic contaminants are displaced, leaving only the more acidic contaminants bound thereto. In most cases, this is a loading far in excess of the column manufacturers recommendations. The chromatographic separation of the more acidic contaminants from the HbAo is thus achieved at this stage.

The feed of the impure hemoglobin solution is conducted at a slow linear flow rate, not greater than 10 cm per minute, and preferably at about 1 cm per minute. This permits kinetic equilibration of the column. The feed concentration range is not critical, but is suitably in the range 0.1–20%, preferably 2–7%.

The achievement of the overload condition can be monitored by analysis of the eluent from the column—when the composition of the eluent shows none, or only traces, of acidic impurity, the maximum practical loading of the column has been achieved.

FIG. 1 of the accompanying drawings diagrammatically illustrates the anionic exchange process portion of the present invention. The ion exchange column 10 having chemical groups, —$N^+R_3$ (typical of anionic exchange resins, but exemplary only), shown at stage A of the process In FIG. 1 is fed with a solution 12 containing a mixture of species represented by stars, for the more acidic contaminants, elipses representing HbAo, and rectangles representing the more basic contaminants. At capacity loading, stage B, substantially all the active chemical groups N—$R_3$ of the column have bound by electrostatic charge to one of the species contained in the mixture.

More solution 12 is fed to the capacity loaded column 10 to reach an overload condition, illustrated in stage C of FIG. 1. Now, all of the more basic contaminants (rectangles) and some of the HbAo (represented by elipses) are displaced therefrom by the more acidic component (represented by stars), which exhibits the greater affinity for the column under these conditions. Feed of solution 12 to the overloaded column continues, to reach stage D illustrated on FIG. 1, at which the acidic species has displaced substantially all of the HbAo from the column, because of its greater affinity under the chosen conditions. Now the eluent 14 issuing from the column contains substantially no detectable amounts of the acidic contaminants. A fairly pure solution of HbAo, but still containing some more basic species, is thus obtained.

The second stage of the preferred process of the present invention uses a cationic exchange column, and is fed with eluent from the first column, to a similar overloaded condition. The desired HbAo and other, unwanted, more basic, impurities are bound in overloaded amounts. The same impure hemoglobin solution from the first column continues to be fed to the second column. Relatively slow feed rates are again employed, suitably 10 cm/min or less, and preferably about 1 cm/min, to permit kinetic equilibration of the solid phase and 10 the liquid phase. The pH of the eluent from the first column is suitably adjusted to the range pH 5–9, preferably pH 6.5–8.5, and most preferably pH 7–8, prior to its entering the cationic exchange column. Low ionic strength of the solution is used, i.e. conductivity less than 3 mS preferably less than 1 mS conductivities as large as 2.5 mS are only useful if very slow flow rates and very high feed dilutions are used. Again, overload conditions are used. The proteinaceous contaminants of higher affinity, i.e. those more basic than HbAo, displace the HbAo from the column, and the HbAo is thus eluted and recovered in exceptionally pure form.

Figure 2:
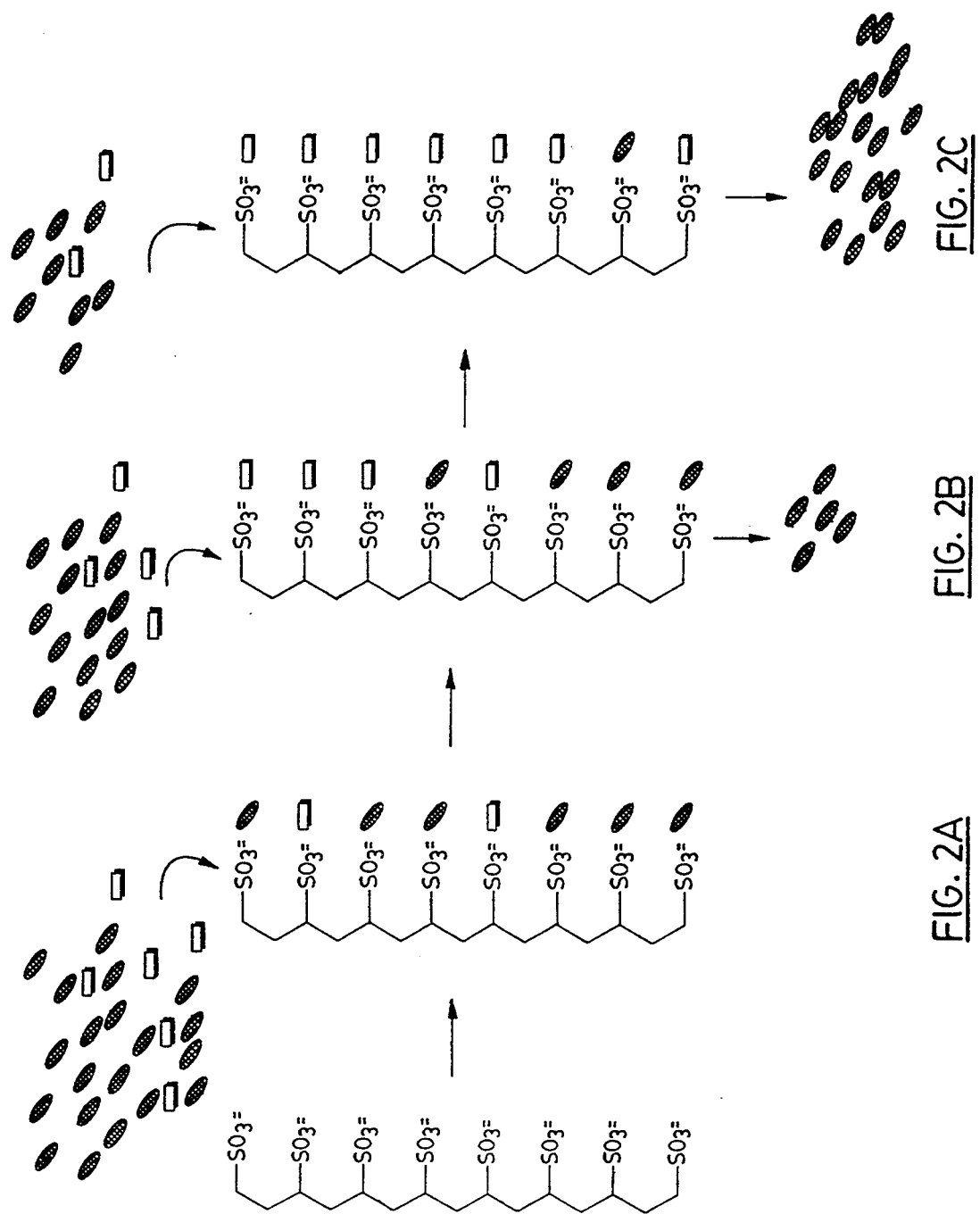
FIGS. 2A–2C are similar illustrations of the second, cationic portion of the preferred process of the present invention.

FIG. 2 of the accompanying drawings diagrammatically illustrates, in a manner similar to FIG. 1, the portion of the process taking place in the cationic exchange column 16. The eluent solution 14 from the first column 12, after suitable pH adjustment, is fed to the column, and initially, in stage A, capacity loading is achieved with both the HbAo (elipses) and the more basic contaminants (rectangles) binding to the chemical groups on the column electrostatically. Whilst these are illustrated as sulfonic groups, other alternatives such as carboxyl groups could equally well be chosen. Feed of eluent solution to the column continues to achieve an overload condition illustrated in stage B of FIG. 2, in which the more basic contaminant, on account of its greater affinity for the column under these conditions, is replacing the HbAo on the column. By continuing the feed to the overloaded column, as illustrated at stage C on FIG. 2, almost 100% pure HbAo is thus displaced and obtained in solution as the eluent from the column.

The higher the column loading accordingly, the higher the percentage recovery of purified HbAo from the column. The eluent is monitored to detect the initial presence of basic species (rectangles) in the eluent, indicating no further recovery of HbAo by displacement from the column, and stopped at that point.

For both the first column and the second column, the flow rates of the impure hemoglobin solution should be optimized for the selected concentration of the impure hemoglobin solution. Linear flow rates of 1 cm/min or less are optimal for hemoglobin solutions at the more concentrated range of 2-6%. Flow rates as high as 2 cm/min can be successfully applied to the resolution of dilute solutions (less than 1% Hb). Resolution for ion exchange chromatography at low loading capacities is usually insensitive to linear flow rate; however, for the process of the present invention, kinetic equilibration during chromatography is highly dependent on flow rate. The concentration of the feed, however, is not critical in either stage.

With the displacement chromatography method of the present invention, using firstly anionic exchange chromatography to remove more acidic components and secondly cationic exchange chromatography to remove more basic components, one can achieve high yields of exceptionally pure HbAo, on a commercial scale. The purities as assayed by analytical anion exchange chromatography are in excess of 99%, and commonly in excess of 99.5%. The effective capacities of the stages are at least an order of magnitude greater than the capacities observed by normal chromatographic approaches. In addition to removal of non-proteinaceous contaminants, the process of the invention also allows substantially complete removal of modified and other unwanted forms of hemoglobin, to leave substantially pure (>99.5%) HbAo. Moreover, as described in more detail below, substantially complete removal of viral particles, active or inactivated, can also be achieved.

The scale-up advantages of the process of the present invention, as compared with a process using standard ion exchange adsorption/elution chromatography, are demonstrated in the following Table 1. The figures in the "Self Displacement" column are derived from the working examples of the process of the present invention, described below. Those in the column "Adsorption/Elution" are obtained from the aforementioned Christensen et al. paper, "Preparation of Human Hemoglobin Ao For Possible Uses of Blood Substitute", J. Biochem Biophys. 17 (1988) 143-154.

TABLE 1

OPERATING PARAMETERS FOR HEMOGLOBIN AO PURIFICATION USING ADSORPTION/ELUTION CHROMATOGRAPHY * vs SELF DISPLACEMENT CHROMATOGRAPHY

|  | SELF DISPLACEMENT | ADSORPTION/ ELUTION |
|---|---|---|
| Column Volume | 5 and 3 L | 51 L |
| Column Capacity | 200-300 mg/ml | 20 mg/ml |
| g Hb Loaded | 1234 | 1754 |
| % Recovery | 81 | 57 |
| g Hb Collected | 1000 | 1000 |
| Buffer Volume For Run and | 132 L | 935 L |

*Christensen, S. m., Median, F., Winslow, R. W., Snell, S. M., Zegna, A. and Marini, M. A. Preparation of Human Hemoglobin Ao For Possible Use as a Blood Substitute. J. Biochem. Biophys. 17 (1988) 143-154.

It is clear from the these figures that the process of the present invention can be run faster, with reasonably small column sizes. It can be run under low pressure conditions and at ambient temperatures. Effective loading capacities which are 10-20 times the capacities reported for conventional chromatographic processes can be attained, making possible the use of relatively small column volumes. This leads to reductions in water requirements, reduced waste disposal and reduced buffer requirements, all of which improve significantly the commercial economics of the process.

The purified hemoglobin solution constituting the eluent from the cationic exchange column can be diafiltered into a buffer of choice, and concentrated to the desired HbAo concentration.

As the ion exchange gel material used in the process of the present invention as the stationery phase, there can be used most of the common, commercially available such gels, provided that they can be successfully derivatized to operate in an ion exchange mode under the selected affinity conditions for the species to be separated. Silica gels polysaccharide (e.g. agarose based) gels, crosslinked polystyrene gels and the like can be used. Specific examples of such gels include those sold under the trade-marks POROS-HQ, an anionic gel, and POROS-HS, a cationic gel, based on DVB-crosslinked polystyrene, and those sold under the trademarks SEPHAROSE, which are based on agrose.

The process of the invention can also be operated to produce an HbAo solution of at least 99.5% purity, and, unexpectedly, free from viral particles, active or inactivated, especially lipid encapsulated viruses such as HIV, herpes simplex virus (HSV) and bovine diarrhea virus, which in many instances is a model for human hepatitis virus, some of the most serious and troublesome blood contaminating viruses. This is a very significant, added advantage to be derived from the use of the present invention, and one which could not have been predicted before the process was tried and the results analyzed. While preferred processes according to the invention involve a step of pasteurization to inactivate viruses, prior to purification, as described above, the achievement of viral particle removal as part of the purification process is especially advantageous. It removes from the blood substitute material any active viral particles which may have survived the pasteurization, and any residual inactivated viral particles. All this can be achieved without the use of any additional, specific viral particle removal step, and without the addition of any special reagents or the like for the purpose of viral removal. Substantially complete removal of lipid encapsulated virus can be achieved. A very significant reduction in the quantity of other viruses is also achieved.

The invention is further described, for illustrative purposes, by the following, non-limiting examples.

SPECIFIC DESCRIPTION OF THE MOST PREFERRED EMBODIMENTS

EXAMPLE 1

Ppreparation of Crude Hb Lysate

Ninety-six units (approx. 30L) of packed red blood cells (RBCs) of the same blood type were pooled, and then diluted with 24 L of 0.9% saline solution. This pool was then filtered through 20μ and 8μ polypropylene filters to remove any residual leukocytes.

After leukocyte filtration, the RBCs were washed with 6 volumes of 0.9% saline in a constant volume diafiltration using 3.5 m² of 0.3 μ Sepracor polyethersulphone hollow fibre membranes. The washing buffer was then replaced with 50 mM Tris lysing buffer, and the RBCs were gradually lysed into 6 volumes of this lysing buffer.

The crude lysate was collected and concentrated from approximately 2.5% Total Hemoglobin (THb) to approximately 9.0% THb using a 30K Molecular Weight Cut Off (MWCO) Millipore PTTK membrane. Once concentrated, the tank was charged with CO gas to convert the hemoglobin to COHb form. The lysate was pasteurized at 62±2° C. for 10 hours in a jacketed tank. The pasteurized lysate was cooled and then centrifuged. Further depth filtration through Millipore 0.8 μ filters prepared the pasteurized lysate for diafiltration on another Millipore 30K PTTK membrane. The material was diafiltered with 5 mM Tris, pH 8.9 until its conductivity was <0.3 mS and the pH was 8.9±0.2. It was then diluted to 4.5-5% THb, at which point it was ready for subsequent chromatographic purification.

EXAMPLE 2-

Self-Displacement Chromatography of Anion Exchange Resin

A 1×10 cm column packed with the anionic exchange resin PerSeptive Poros HQ-50 was washed with 4 column volumes of 1N NaCl and equilibrated with 5 mM Tris buffer, pH 8.8. After equilibration 50 ml of a 3.0% (3 g/100 ml) crude hemoglobin lysate (~85% HbAo) in 5 mM Tris, prepared as described in Example 1, pH 8.8, was loaded onto the column at 0.78 ml/min (1 cm/min). This led to an eventual overload of the column—200 mg of the solute loaded per ml of resin, compared with the manufacturer's stated loading capacity of 50 mg/ml. The eluent was collected. The column was then washed with 2 column volumes of 5 mM Tris, pH 8.8 buffer and this eluent was pooled with eluent collected during loading. The column was then washed with 1N NaCl to elute the retained proteins, and this was discarded. The column was regenerated using 3 column volume 0.5 N HCl and 4 column volume 1 M NaOh. The hemoglobin eluent from the anion-exchange resin was analyzed on an analytical anion-exchange column using a pH gradient, as described in more detail below, in Example 11. It was determined to be about 95-96% HbAo, as shown on FIG. 3, with recovery of 90% of the HbAo loaded on to the column.

EXAMPLE 3

Self-Displacement Chromatography on Anionic Exchange Resin

Figure 3:
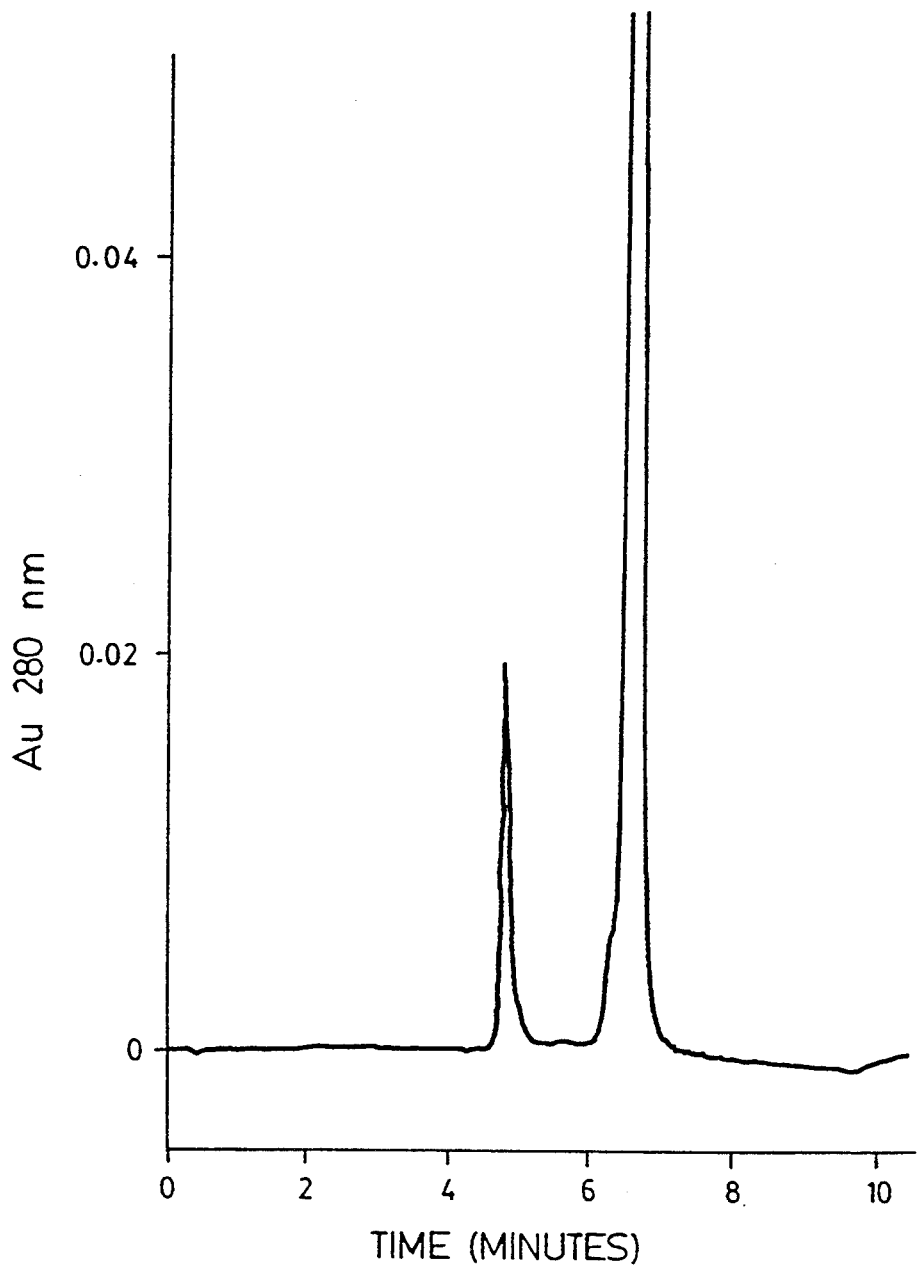
FIG. 3 is an anion exchange chromatogram derived from the results of Examples 2 and 3 below.

A 1×10 cm column packed with Merck Fractogel-TMAE was washed with 4 column volumes of 1N NaCl and equilibrated with 5 mM Tris buffer, pH 8.8. After equilibration 50 ml of a 3.0% (3 g/100 ml) crude hemoglobin lysate (−85% HbAo) in 5 mM Tris, prepared as described in Example 1, pH 8.8, was loaded onto the column at 0.78 mL/min (1 cm/min). This similarly led to an eventual overload of the column. The eluent was collected. The column was then washed with 2 column volumes of 5 mMTris, pH 8.8 buffer and this eluent was pooled with eluent collected during loading. The column was then washed with 1N NaCl to elute the retained proteins, and this was discarded. The column was regenerated using 3 column volume 0.5 N HCl and 4 column volume 1 M NaOH. The hemoglobin eluent from the anion-exchange resin was analyzed on an analytical anion-exchange column using a pH gradient, as described in more detail below in Example 11, determined to be about 95-96% HbAo, as shown in FIG. 3, with a recovery of 73% of the HbAo loaded on to the column.

EXAMPLE 4

Self-Displacement Chromatography on a Cation-Exchange Resin

Figure 4:
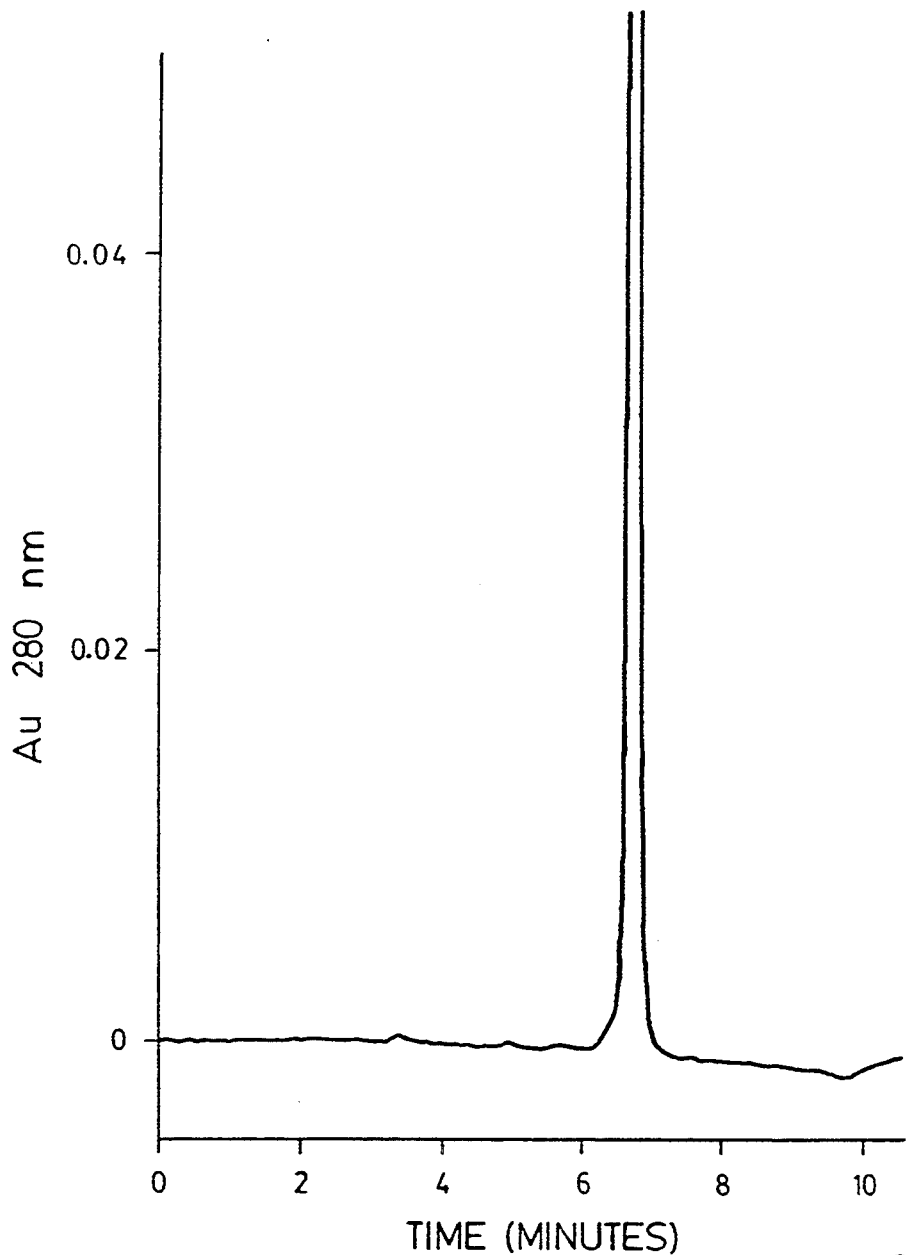
FIG. 4 is an anionic exchange chromatogram derived from the results of Example 4 below.

A 1×10 cm column packed with Perseptive Poros HS-50 was washed with 4 column volumes of 1N NaCl and equilibrated with 5 mM Tris buffer, pH 7.5. After equilibration 120 ml of a 2.0% (2 g/100 ml) anion-exchange purified hemoglobin ~95% HbAo) in a 5 mM Tris, prepared as described in Examples 2 and 3, pH 7.5 buffer, was loaded onto the column at 0.78 ml/min (1 cm/min). This led eventually to a substantial overload of the column, to the extent of about 5 times the manufacturer's recommendation. The eluent was collected. The column was then washed with 2 column volumes of 5 mM Tris, pH 7.5 buffer and this eluent was pooled with eluent collected during loading. The column was then washed with 1N NaCl to elute the retained proteins, and thi was discarded. The column was regenerated using 3 column volume 0.5 N HCl and 4 column volume 1 M NaOH. The hemoglobin eluent from the anion-exchange resin was analyzed on an analytical anion-exchange column using a pH gradient, and was determined to be >99% HbAo, as shown on FIG. 4, with a recovery of about 90% of the HbAo loaded on to the column.

EXAMPLE 5

The effect of conductivity on the self-displacement chromatography on an anion-exchange resin (first stage) was studied.

Effective displacement chromatography is critically dependent on the ionic strength of buffer and/or sample, as determined by conductivity. The experiment summarized below in Table 2 was performed feeding crude lysate of Example 1 to the Poros HQ-50 anion exchange resin from PerSeptive Biosystems Inc. The eluent from the column was analyzed by analytical anionic exchange chromatography. The fraction obtained during run no. 1 were all free from detectable contaminants, whereas even the first fraction from run 2 was contaminated with acid contaminants.

TABLE 2

| Run | Load mg/ml | THb | pH | Ms | Column (L × D) | Buffer | Flow Rate (cm/min) | Purification |
|---|---|---|---|---|---|---|---|---|
| 1 | 200 | 3.0 | 8.8 | 0.2/0.4 | 10 × 1 | Tris | 1 | 100% |
| 2 | 200 | 2.8 | 8.8 | 2.85 | 10 × 1 | Tris | 1 | 0% |

EXAMPLE 6

Overloading the column achieves a higher recovery of purified HbAo. The experiments reported below in Table 4 demonstrate a very high overload on a 10 ml column of cationic exchange Poros HS-50 resin, which ensures all of the binding sites are occupied by the contaminants, allowing a higher recovery of purified HbAo. The overload in the first experiment was 13.5 times the manufacturer's recommendation. That in the second experiment was about 5 times the manufacturer's recommendation. The higher overloading leads to a significant improvement in recovery of HbAo from the column.

TABLE 3

| Load | THb | pH | mS | Column (L × D) | Buffer | Flow Rate cm/min | Freedom From Acidic Contaminants |
|---|---|---|---|---|---|---|---|
| 216 | 2.9 | 7.4 | 0.6 | 9.5 × 1 | Tris | 0.6 | 100% 77% Rec |
| 308 | 3.1 | 7.5 | 0.5 | 9.5 × 1 | Tris | 0.6 | 100% 88% Rec |

EXAMPLE 7

Comparison Between Small and Large Columns

The displacement chromatography process of the present invention can be used on small and large columns. Using anionic exchange resin Poros HQ-50 and cationic exchange resin Poros HS-50 sequentially, this comparison was done utilizing a 15 and 10 liter column respectively with 10 ml columns. The feed solution to the Poros HQ-50 column was prepared as described in Example 1. The eluent from the HQ-50 column was fed to the HS-50 column. Table 4 shows the conditions and results of the use of the Poros HQ-50 columns. Table 5 shows the results of the use of the HS-50 column. The results show that both stages of the process can be scaled up to at least 10–15 liter column size, for commercialization.

TABLE 4

| Amount loaded | Load mg/ml | THb | Ph | Ms | Column L × S | Buffer | Flow Rate cm/min | Purity* |
|---|---|---|---|---|---|---|---|---|
| 1.6 g | 210 | 5.6 | 8.9 | 0.5 | 10 × 1 | Tris | 1 | 100% |
| 3.2 kg | 200 | 4.7 | 8.8 | 0.3 | 10 × 45 | Tris | 1 | 100% |

TABLE 5

| Amount loaded | Load mg/ml | THb | Ph | Ms | Column L × S | Buffer | Flow Rate cm/min | Purity* |
|---|---|---|---|---|---|---|---|---|
| 2.4 g | 308 | 3.1 | 7.5 | 0.5 | 9.5 × 1 | Tris | 0.6 | 100% |
| 1.7 kg | 254 | 3.7 | 7.6 | 0.4 | 9.5 × 30 | Tris | 0.6 | 100% |

EXAMPLE 8

Analysis of Crude Hemoglobin Lysate and Purified Hemoglobin by Isoelectric Focusing (IEF)

Figure 5:
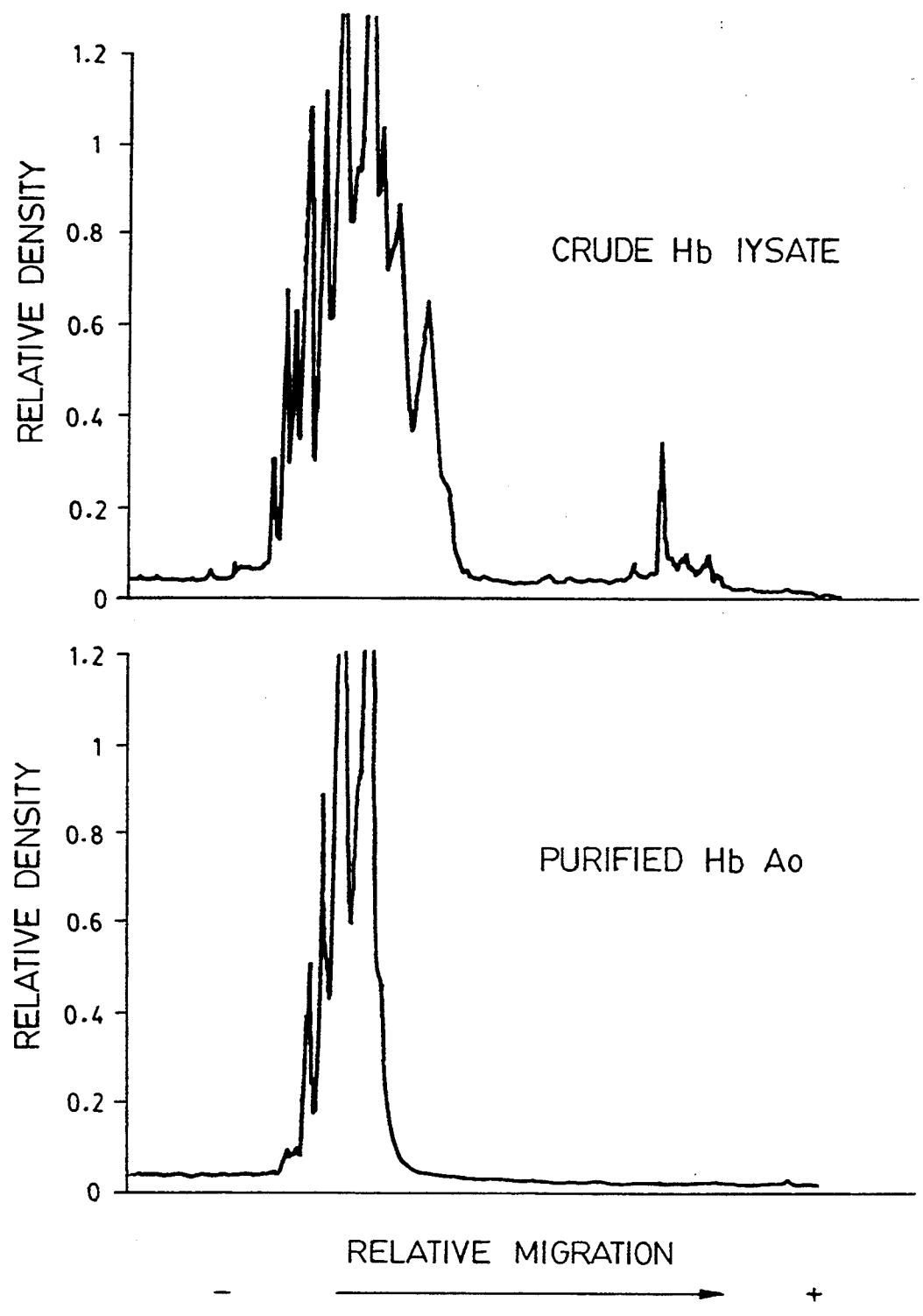
FIG. 5 is an graphical presentation of the results of Example 8 below.

Isoelectric focusing (IEF) analysis was performed using an agarose based gel into which a stable pH gradient was established using commercially available ampholytes. The ampholytes used were such that 90% of them were in the pH 5–8 range and 10% were in the pH 3.5–10 range. The agarose in the gel was at a final concentration of 1.25% and the ampholytes were present at a final concentration of about 2%. For the purpose of assessing purity, the gels were grossly overloaded (1 mg protein was loaded per lane). Electrophoresis was performed at low current settings to ensure that the proteins migrate as a uniformly straight band. After a steady state was reached, the voltage and the current was increased for a short period to sharpen the bands further. After electrophoresis, the proteins in the agarose gel were fixed using trichloroacetic acid and sulfosalicylic acid solution. After the fixation step, the gel was stained with Comasie-Blue to visualize the protein bands. For scanning purposes, the gel was air dried, and then a laser densitometer was used to obtain tracing of the electrofocussed lanes containing crude hemoglobin lysate and purified hemoglobin. FIG. 5 shows a comparison between the IEF of crude hemoglobin lysate, prepared as described in Example 1, and purified HbAo prepared according to the invention. Purification of the hemoglobin solution was conducted using sequentially a Poros HQ-50 column as described in Example 2, and a Poros HS-50 column as described in Example 4.

EXAMPLE 9

Immuno-Analysis of Crude Hemoglobin Lysate and Purified Hemoglobin

To analyze the amount of various contaminants in the crude hemoglobin lysate from Example 1 and purified hemoglobin, prepared according to the process of the invention, the technique of immunostaining was employed. After the electrofocusing of proteins on the agarose gel, the proteins were transferred onto a nitrocellulose paper using capillary blotting. The remaining free binding sites on the paper were blocked by incubating the blot in hydrolyzed fish gelatin solution. After the incubation in the blocker, the blot was washed with tris-buffered saline (TBS) and then incubated with the primary antibody. (The primary antibody is the antibody against which the sample is to be tested, e.g. anti-human serum albumin (anti-HSA) would be used to test for HSA in the hemoglobin solutions). After this incubation, the blot was washed with TBS and then incubated with the secondary antibody, conjugated to a marker enzyme (e.g. Horse radish peroxidase), which is antibody against eh primary antibody. After incubation with the secondary antibody, the blot is washed with TBS again, and then a substrate for the marker enzyme is added. A coloured precipitate will appear where the secondary antibody has bound to the primary antibody, which has bound to its antigen, thus indicating the amount and position of the antigen to the primary antigen on the IEF gel.

The results are shown in Table 7 below, on which "++++++" indicates a strong signal, "+" indicates a barely detectable signal, and "−" denotes no signal detected.

TABLE 6

| Antibody used | Crude Hb lysate | Hemoglobin |
|---|---|---|
| Human Serum Albumin | ++++++++++ | $+^a$ |
| Red Blood Cell (RBC) | +++++++ | $+^b$ |
| RBC membrane | +++++ | − |
| Human Plasma | ++++++++++ | $+^c$ |
| Carbonic Anhydrase I | +++ | − |
| Spectrin | ++++ | − |
| Glycophorin | ++ | − | a. Using HSA standards on the immunoblots, the amount of HSA present in the purified HbAo was estimated at <5 pg/mg Hb (<50 ppm).

b. A trace contaminant with a pI ~5.2 was detected which cross-reacts with anti-RBC antibody. Other researchers have also reported a similar protein in their purified Hb solutions—see Christensen et al., op. cit.

c. Anti-HSA antibody present in the anti-human plasma detected the HSA present in the purified HbAo.

EXAMPLE 10

Human Serum Albumin—Immuno Detection (HSA-ID)

A chromatographic method was used to quantitate the amount of HSA present in the hemoglobin solutions. The method used an antibody (anti-HSA) covalently bound to a matrix in a column. When sample is injected onto the column, everything but the antigen for the antibody (HSA) passes through during the load/wash step. Upon using the elute buffer the bound antigen (HSA) elutes from the column and the area of the peak is used to quantitate the antigen present in the sample.

The immunodiffusion (ID) cartridge used for the assay was from PerSeptive Biosystems. The flow rate used for the assay was 2 ml/min. The cartridge-shaped column (1.6 mmD × 26 mmL) was equilibrated with the loading buffer (10 mM phosphate buffer +300 mMNaCl, pH 7.2), and then 50 μl of the sample was injected. The loading buffer was used to wash the column for 0.25 minutes, and then the elute buffer was used (for 3.5 minutes) to elute the bound HSA from the column. The column was then re-equilibrated with the loading buffer for the next injection. Using this method, the amount of HSA present in the purified hemoglobin was estimated to be around 0.005% relative to hemoglobin.

EXAMPLE 11

Analytical Anion Exchange Chromatography

The chromatographic method used to analyze the purity of hemoglobin in the products of Examples 2 and 4, was as follows. The assay was based on loading sample on to an anion-exchange column at high pH (pH 8.5), such that all the protein bound to the column, and then a pH gradient from pH 8.5 to pH 6.5 was used to sequentially elute the proteins from the column. Using this chromatographic assay, very similar proteins (e.g. various hemoglobin variants) could be neatly separated. A 4.6 mm × 100 mm analytical anion exchange column from PerSeptive Biosystems was used for the assay. The buffers used were A) 25 mM Tris+25 mM Bis-tris, pH 8.5 and B 25 mM Tris+25 mM Bis-tris, pH 6.5. The whole assay was performed at the flow rate of 5 ml/min. After the column was equilibrated with buffer B, 10 μl sample (conc. 10 mg/ml) was injected on to the column, and the gradient (100% buffer B to 100% buffer A over 25 column volume) was started. FIG. 3 shows the chromatographic profile of anion-exchange purified hemoglobin (Example 2 product) and FIG. 5 shows the purified HbAo (Example 4 product) when analyzed by this assay.

EXAMPLE 12

Virus Removal

The process of the present invention was tested for its ability to remove viruses from the crude hemoglobin To samples of a crude lysate prepared as described in Example 1, and to samples of partially purified hemoglobin solution issuing from the anionic column, i.e. the product from Examples 2 and 3, test quantities of the following viruses were added, in active form:
Poliovirus Type 1
Human Immunodeficiency (HIV)
Bovine Diarrhea Virus (which is a model for the human hepatitis virus)
Herpes Simplex Virus Type 1 (HSV-1).

Aliquots of the eluents from the respective columns were added to test cell systems, in the cases of poliovirus, herpes virus and bovine diarrhea virus with which the active virus present interacts to give plaques. Known, standard assays were conducted. In the case of HIV, the aliquots were added to tissue culture media. The amount of virus present was determined by a change in the growth of the cell line. This change is known as $TCID_{50}$ (tissue culture infectious dose endpoint at 50%). The results are reported in Table 7 below.

TABLE 7

| | LOG REDUCTION VIRUS ACHIEVED THROUGH CHROMATOGRAPHY | | | |
|---|---|---|---|---|
| Virus | Poliovirus Type 1 | Human Immuno-Deficiency | Bovine Virus Diarrhea | Herpes Simplex |
| Genome | RNA | RNA | RNA | DNA |
| Enveloped | No | Yes | Yes | Yes |
| Test System | Vero Cells | MT-4 Cells | EBTr Cells | Vero Cells |
| Anion Load | $1.4 \times 10^7$ pfu/ml | $1.4 \times 10^5$ $TCID_{50}$/ml | $1.7 \times 10^5$ pfu/ml | $5.3 \times 10^6$ pfu/ml |
| Anion Eluate | $8.5 \times 10^6$ pfu/ml | $<3$ $TCID_{50}$ ml | $<20$ pfu/ml | $<3$ pfu/ml |
| Log Reduction | $<1$ | $>5$ | $<20$ pfu/ml | $>6$ |
| Cation Load | $3.1 \times 10^7$ pfu/ml | $3.2 \times 10^5$ $TCID_{50}$/ml | $2.8 \times 10^5$ pfu/ml | $2.0 \times 10^6$ pfu/ml |
| Cation Eluate | $7.5 \times 10^6$ pfu/ml | $5.6 \times 10^2$ $TCID_{50}$ ml | $2.1 \times 10^4$ pfu/ml | $4.1 \times 10^3$ pfu/ml |
| Log Reduce | $<1$ | $>3$ | $>1$ | $>3$ |

These results show a significant reduction in the amount of polio virus, using either the anionic exchange self-displacement or the cationic exchange self-displacement steps of the present invention, and a remarkable reduction in the cases of HIV, HSV and bovine diarrhea. This completely unexpected, but presents a significant advantage of the use of the present invention.

We claim:

1. A process of separating a preselected hemoglobin from a crude solution thereof which also contains contaminating proteinaceous substances, said process comprising:
in a first chromatographic stage, feeding the crude solution to a chromatographic column and subjecting it to chromatography under either anionic exchange conditions under which components of the crude solution more acidic than said preselected hemoglobin have preferential binding affinity thereover, or to cationic exchange conditions under which components of the crude solution more basic than said preselected hemoglobin have preferential binding affinity thereover;
continuing the feed of the crude solution in the first chromatographic stage until the column is substantially fully loaded with hemoglobin species and components of greater affinity;

further continuing the feed of the crude solution in the first chromatographic stage to cause column overload and subsequent displacement of the hemoglobin species therefrom;

in a second chromatographic stage, feeding the hemoglobin species-containing eluent from the first stage to a chromatographic column and subjecting it to chromatography under said anionic exchange conditions or cationic exchange conditions not selected for said first stage;

continuing the feed of said eluent in the second chromatographic stage until the column is substantially fully loaded with hemoglobin species and components of greater affinity under said second stage conditions;

further continuing the feed of said eluent in the second chromatographic stage to cause column overload and consequent displacement of the hemoglobin species therefrom.

2. The process of claim 1 wherein the first stage is anionic exchange chromatography, and the second stage is cationic exchange chromatography.

3. The process of claim 2 wherein the preselected hemoglobin species is normal adult human hemoglobin HbAo.

4. The process of claim 3 wherein the first stage anionic exchange process is conducted at pH 5–9 and using a feed solution of low conductivity, less than 3 mS.

5. The process of claim 4 wherein the first stage anionic exchange process is conducted at pH 6.5–8.5 and using a feed solution of conductivity less than 1 mS.

6. The process of claim 4 wherein the feed solution is fed to the column at a rate not greater than 10 cm per minute.

7. The process of claim 6 wherein the feed solution concentration is in the range 0.1–20%.

8. The process of claim 4 wherein the second stage, cationic exchange chromatography is conducted at pH 6.5–8.5 using a feed solution of conductivity less than 3 mS.

9. The process of claim 8 wherein the second stage, cationic exchange chromatography is conducted at pH 7–7.5 using a feed solution of conductivity less than 1 mS.

10. The process of claim 8 wherein the feed solution is fed to the second stage, cationic exchange column at a rate not greater than 10 cm per minute.

11. The process of claim 8 wherein concentration of the feed solution to the second stage cationic exchange column is from 2–6%.

* * * * *

UNITED STATES PATENT AND TRADEMARK OFFICE
CERTIFICATE OF CORRECTION

PATENT NO. : 5,439,591
DATED : August 8, 1995
INVENTOR(S) : Pliura, et al.

It is certified that error appears in the above-identified patent and that said Letters Patent is hereby corrected as shown below:

Column 16, line 5, delete "5-9" and insert --7-10--.

Column 16, line 8, delete "6.5-8.5" and insert --8.5-9.0--.

Signed and Sealed this

Ninth Day of December, 1997

Attest:

BRUCE LEHMAN

*Attesting Officer*     *Commissioner of Patents and Trademarks*